US009448397B2

(12) United States Patent
Makiyama et al.

(10) Patent No.: US 9,448,397 B2
(45) Date of Patent: Sep. 20, 2016

(54) IMAGE PICKUP UNIT AND ENDOSCOPE

(71) Applicant: OLYMPUS CORPORATION, Tokyo (JP)

(72) Inventors: Satoshi Makiyama, Hino (JP); Takehiko Iguchi, Hino (JP); Shinya Kono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/921,215

(22) Filed: Oct. 23, 2015

(65) Prior Publication Data

US 2016/0041381 A1   Feb. 11, 2016

Related U.S. Application Data

(63) Continuation of application No. PCT/JP2014/061838, filed on Apr. 28, 2014.

(30) Foreign Application Priority Data

Jun. 19, 2013   (JP) .................. 2013-128836

(51) Int. Cl.
*G02B 7/02*     (2006.01)
*G02B 23/24*    (2006.01)
(Continued)

(52) U.S. Cl.
CPC ....... *G02B 23/2438* (2013.01); *A61B 1/00096* (2013.01); *A61B 1/00188* (2013.01); *G02B 7/10* (2013.01); *G02B 23/2423* (2013.01); *G02B 23/2476* (2013.01); *A61B 1/0011* (2013.01)

(58) Field of Classification Search
USPC ........... 359/811, 813–15, 819–824; 600/101, 600/117, 118, 145, 164–166, 168
See application file for complete search history.

(56) References Cited

U.S. PATENT DOCUMENTS

2010/0063361 A1   3/2010 Kuchimaru et al.
2013/0107025 A1   5/2013 Kuchimaru
(Continued)

FOREIGN PATENT DOCUMENTS

EP   2161606 A1   3/2010
EP   2296028 A1   3/2011
(Continued)

OTHER PUBLICATIONS

International Search Report dated Jul. 8, 2014 issued in PCT/JP2014/061838.
English Abstract of JP 2008-151988 A, dated Jul. 3, 2008.

*Primary Examiner* — Joseph P Martinez
*Assistant Examiner* — Brandi Thomas
(74) *Attorney, Agent, or Firm* — Scully, Scott, Murphy & Presser, PC

(57) ABSTRACT

An image pickup unit includes: a moving lens holding barrel that holds a moving lens constituting a part of an objective optical system and is disposed so as to freely advance and retract along a shooting optical axis O; a drive unit that generates a driving force for advancing and retracting the moving lens holding barrel along the shooting optical axis O in a fixed barrel; a flexible substrate disposed so as to urge the moving lens holding barrel in one direction orthogonal to the shooting optical axis O and bent so as to press a part of an outer surface of the moving lens holding barrel in the one direction to an inner surface of the fixed barrel; and a magnetism detecting portion detecting a relative position of the moving lens holding barrel from the fixed barrel according to magnetism of a position detecting magnet.

3 Claims, 8 Drawing Sheets

(51) Int. Cl.
    *A61B 1/00*        (2006.01)
    *G02B 7/10*        (2006.01)

(56)            References Cited

U.S. PATENT DOCUMENTS

2013/0314517 A1*  11/2013  Makiyama .............. A61B 1/045
                                                         348/65
2014/0185153 A1*  7/2014   Shibasaki ................ G02B 7/10
                                                        359/823

FOREIGN PATENT DOCUMENTS

| JP | H08-029668 A | 2/1996 |
| JP | 2010-063491 A | 3/2010 |
| JP | 2010-240035 A | 10/2010 |
| JP | 2010-243195 A | 10/2010 |
| JP | 4804325 B2 | 11/2011 |
| JP | 5274733 B1 | 8/2013 |
| WO | WO 2013/054787 A1 | 4/2013 |

\* cited by examiner

IMAGE PICKUP UNIT AND ENDOSCOPE

CROSS REFERENCE TO RELATED APPLICATION

This application is a continuation application of PCT/JP2014/061838 filed on Apr. 28, 2014 and claims benefit of Japanese Application No. 2013-128836 filed in Japan on Jun. 19, 2013, the entire contents of which are incorporated herein by this reference.

BACKGROUND OF THE INVENTION

1. Field of the Invention

The present invention relates to an image pickup unit including a moving lens drive unit that drives a moving lens forward and backward, and an endoscope.

2. Description of the Related Art

Endoscopes provided with image pickup units for picking up optical images are used in, for example, a medical or industrial field. Such an endoscope can be introduced into a living body and a structure from the outside to the inside observe points that are hard to observe in the living body and the structure.

An image pickup unit of an endoscope is provided with an objective lens that forms an object image, and a typical image pickup device, for example, a CCD (charge-coupled device) or a CMOS (complementary metal oxide semiconductor) sensor disposed on an image forming surface of the objective lens.

For example, Japanese Patent Application Laid-Open Publication No. 2010-243195 discloses an endoscope that includes a moving lens holding barrel provided with a moving lens. The endoscope has a function of changing a shooting magnification (scaling function, zooming function) by advancing and retracting the moving lens holding barrel. Japanese Patent Application Laid-Open Publication No. 2010-243195 discloses a technique for an electrostatic encoder that is contained in the endoscope so as to measure either a position or a displacement of the moving lens.

Moreover, Japanese Patent No. 4804325 (Japanese Patent Application Laid-Open Publication No. 2008-151988) discloses a lens barrel including a lens holding member movable in an optical axis direction with respect to a fixed member, and a voice coil motor that drives the lens holding member in the optical axis direction along a guide member, and a technique of urging the lens holding member to the guide member in one direction using leakage flux from a yoke of the voice coil motor.

SUMMARY OF THE INVENTION

An image pickup unit according to an aspect of the present invention is an image pickup unit having an objective optical system that forms an object image, the image pickup unit including: a moving lens constituting a part of the objective optical system; a moving lens holding barrel for holding the moving lens, the moving lens holding barrel being disposed so as to freely advance and retract along a shooting optical axis that enters the objective optical system; a fixed barrel that stores and holds the moving lens holding barrel so as to freely advance and retract; a drive unit serving as a voice coil motor portion that generates a driving force for advancing and retracting the moving lens holding barrel along the shooting optical axis in the fixed barrel, the drive unit including a coil wound about the optical axis around the moving lens holding barrel, and a permanent magnet fixed to the fixed barrel; a flexible substrate for power supply to the drive unit, the flexible substrate being disposed so as to urge the moving lens holding barrel in one direction orthogonal to the shooting optical axis and bent so as to press a part of an outer surface of the moving lens holding barrel in the one direction to an inner surface of the fixed barrel; a position detecting magnet fixed to the moving lens holding barrel; and a magnetism detecting portion opposed to the position detecting magnet with a predetermined clearance in a direction orthogonal to the optical axis, the magnetism detecting portion detecting a relative position of the moving lens holding barrel from the fixed barrel according to magnetism of the position detecting magnet, the flexible substrate urging the moving lens holding barrel in the one direction so as to keep the predetermined clearance between the position detecting magnet and the magnetism detecting portion.

An endoscope according to an aspect of the present invention includes an image pickup unit having an objective optical system that forms an object image, the image pickup unit including: a moving lens constituting a part of the objective optical system; a moving lens holding barrel for holding the moving lens, the moving lens holding barrel being disposed so as to freely advance and retract along a shooting optical axis that enters the objective optical system; a fixed barrel that stores and holds the moving lens holding barrel so as to freely advance and retract; a drive unit serving as a voice coil motor portion that generates a driving force for advancing and retracting the moving lens holding barrel along the shooting optical axis in the fixed barrel, the drive unit including a coil wound about the optical axis around the moving lens holding barrel, and a permanent magnet fixed to the fixed barrel; a flexible substrate for power supply to the drive unit, the flexible substrate being disposed so as to urge the moving lens holding barrel in one direction orthogonal to the shooting optical axis and bent so as to press a part of an outer surface of the moving lens holding barrel in the one direction to an inner surface of the fixed barrel; a position detecting magnet fixed to the moving lens holding barrel; and a magnetism detecting portion opposed to the position detecting magnet with a predetermined clearance in a direction orthogonal to the optical axis, the magnetism detecting portion detecting a relative position of the moving lens holding barrel from the fixed barrel according to magnetism of the position detecting magnet, the flexible substrate urging the moving lens holding barrel in the one direction so as to keep the predetermined clearance between the position detecting magnet and the magnetism detecting portion.

The present invention can achieve a small image pickup unit that can smoothly move a moving lens even with a low-power actuator, and an endoscope including the image pickup unit.

DETAILED DESCRIPTION OF THE PREFERRED EMBODIMENT

Figure 1:
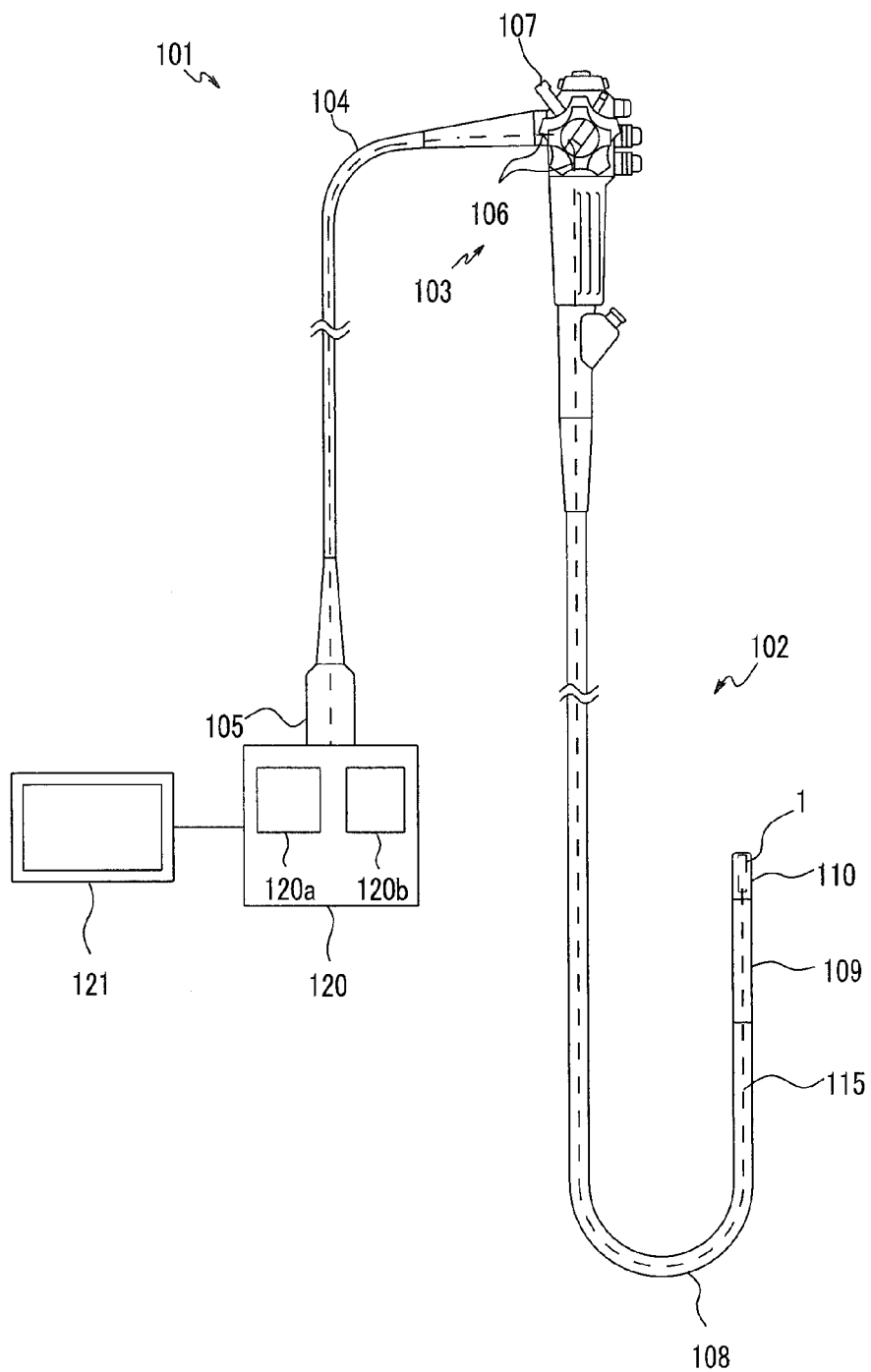
FIG. 1 is a diagram showing a configuration of an endoscope.

A preferred embodiment of the present invention will be described below with reference to the accompanying drawings. Note that in each of the drawings used for the following explanation, components are illustrated with different scales so as to be sized recognizably on the drawings. The present invention is not limited only to the number of components, the shapes of the components, a size ratio of the components, and a relative positional relationship among the respective components on the drawings. In the following explanation, upper and lower parts of the components may be vertically arranged in the drawings.

Figure 2:
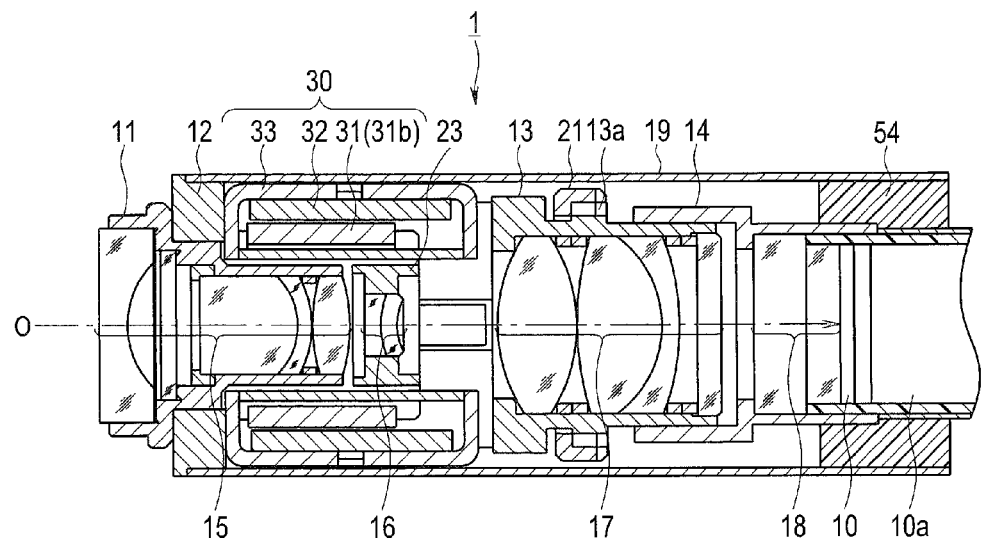
FIG. 2 is a longitudinal section showing a configuration of an image pickup unit in a longitudinal direction.
Figure 3:
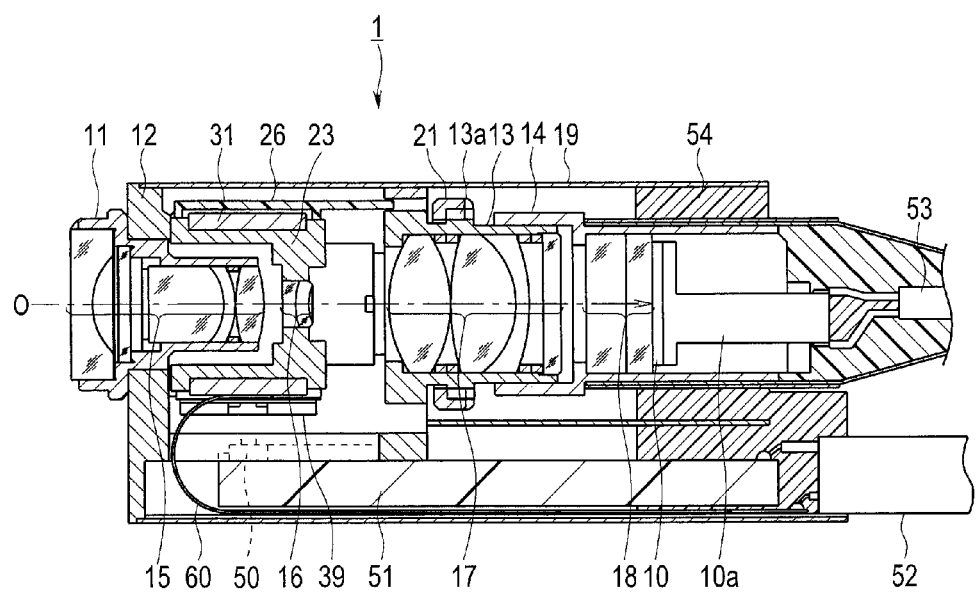
FIG. 3 is a longitudinal section showing the configuration of the image pickup unit in a longitudinal direction different from that of FIG. 2.
Figure 4:
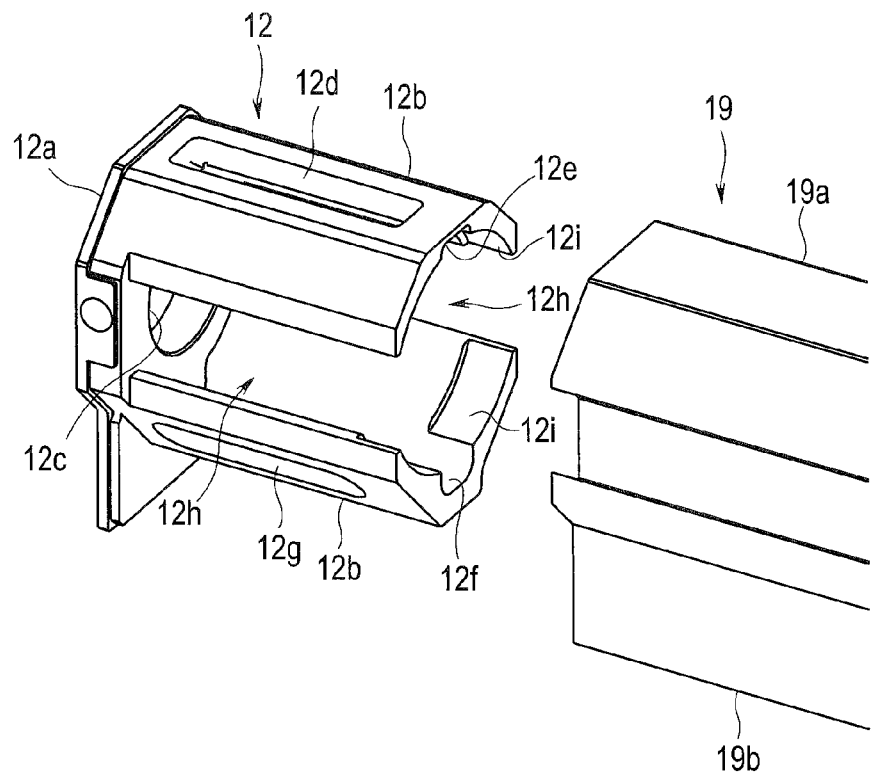
FIG. 4 is a perspective view showing configurations of a fixed barrel and a shield cover.
Figure 5:
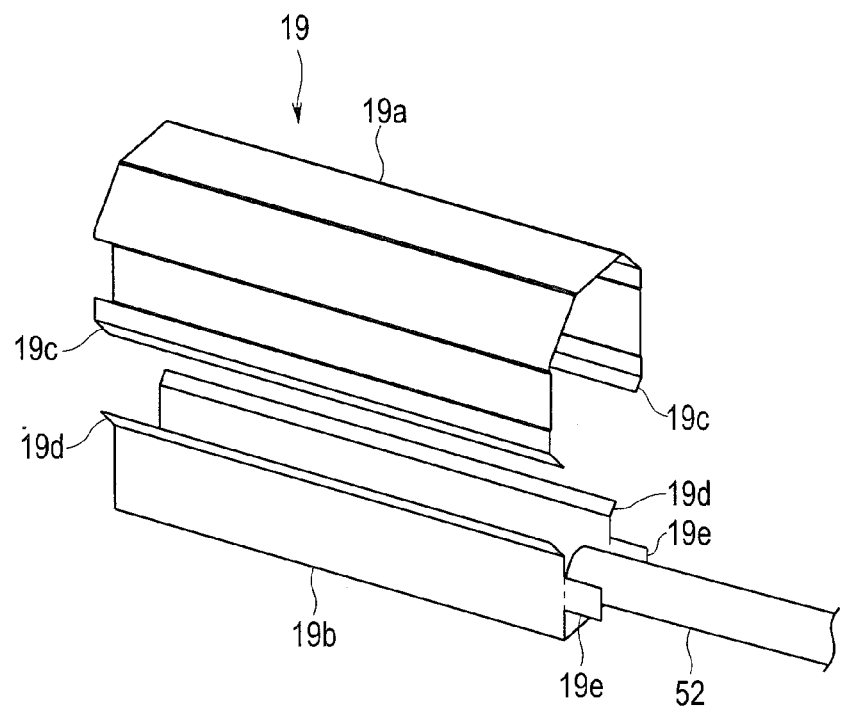
FIG. 5 is a perspective view showing the configuration of the shield cover.
Figure 6:
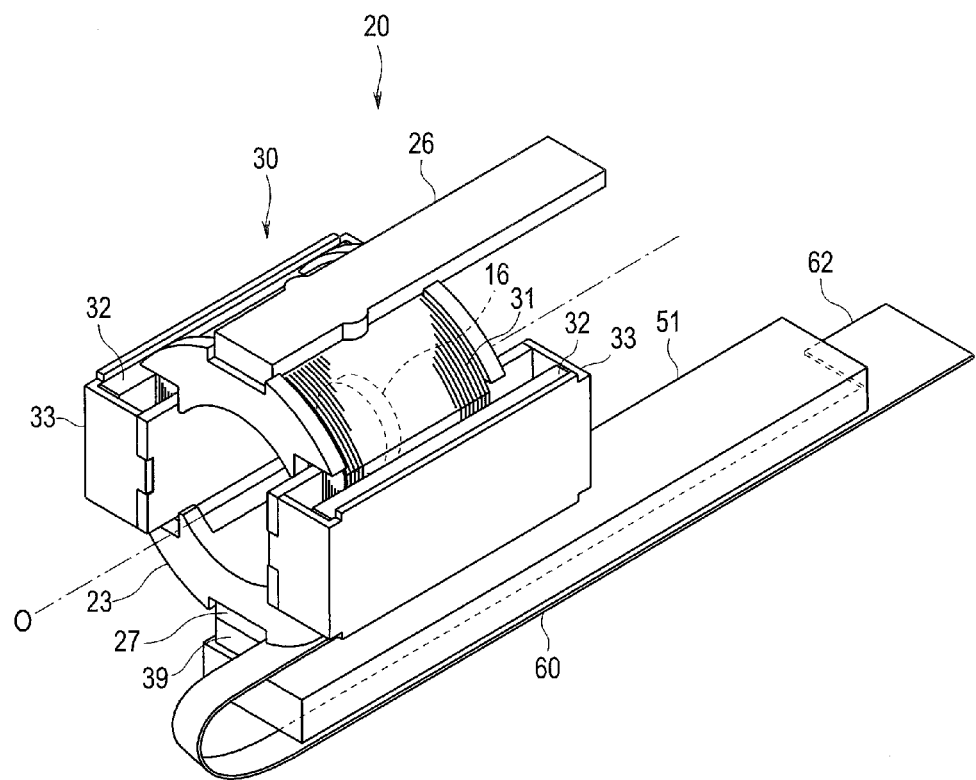
FIG. 6 is a perspective view showing a configuration of a moving lens drive unit.
Figure 7:
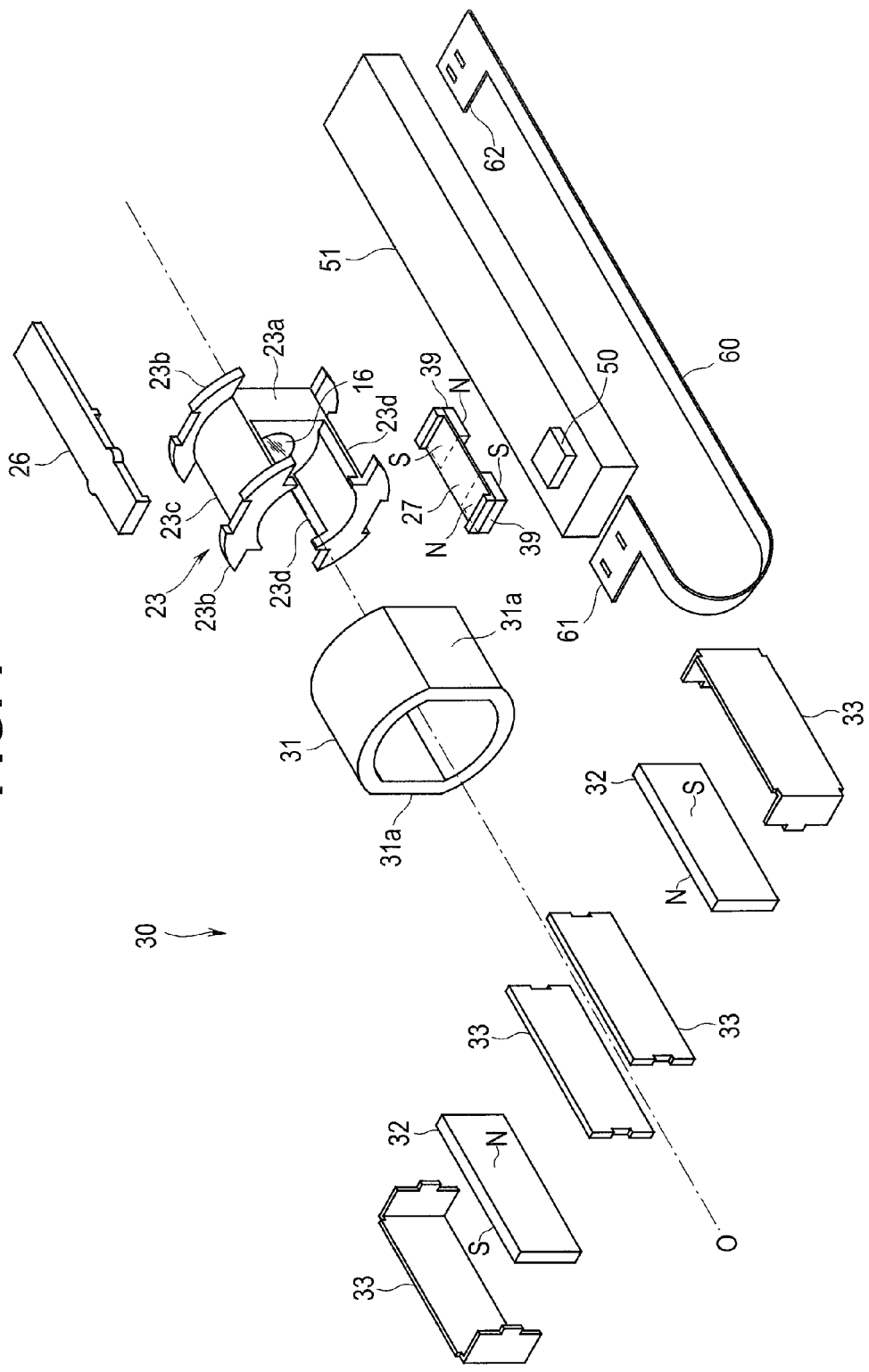
FIG. 7 is an exploded perspective view showing the configuration of the moving lens drive unit.
Figure 8:
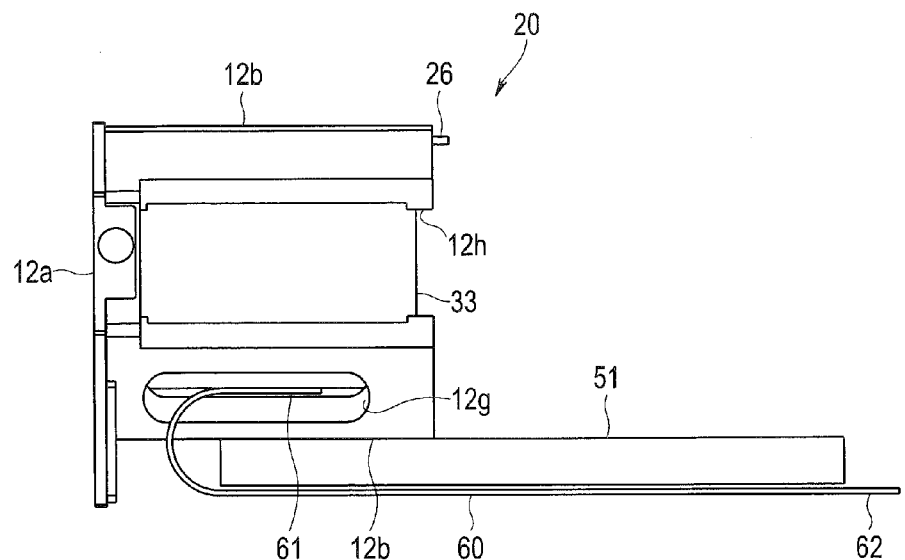
FIG. 8 is a side view showing a state of a moving lens drive unit disposed in the fixed barrel.
Figure 9:
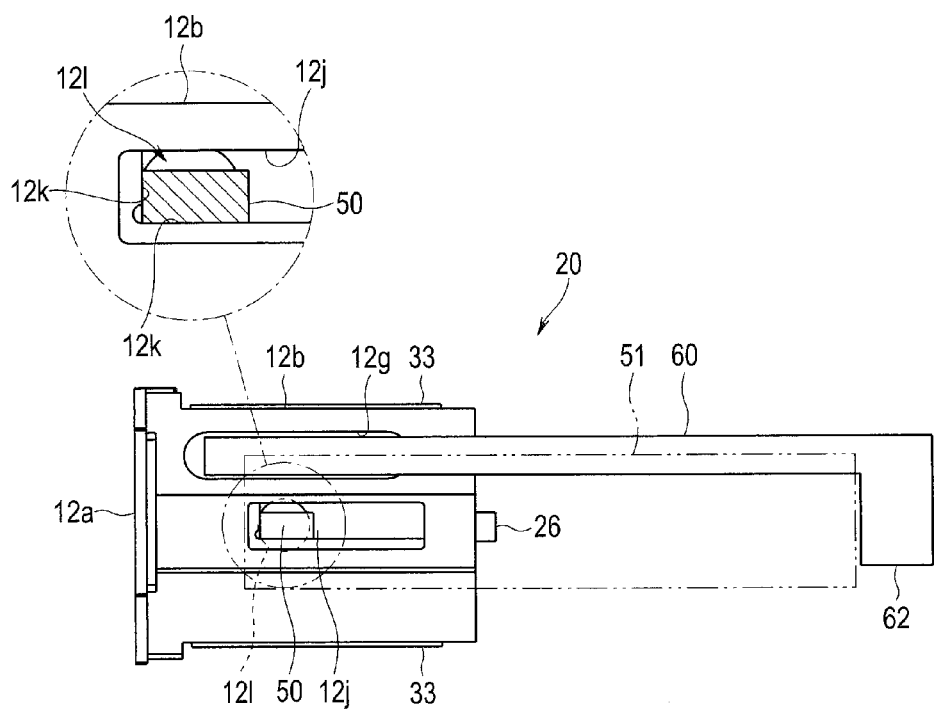
FIG. 9 is a bottom view showing the moving lens drive unit disposed in the fixed barrel.
Figure 10:
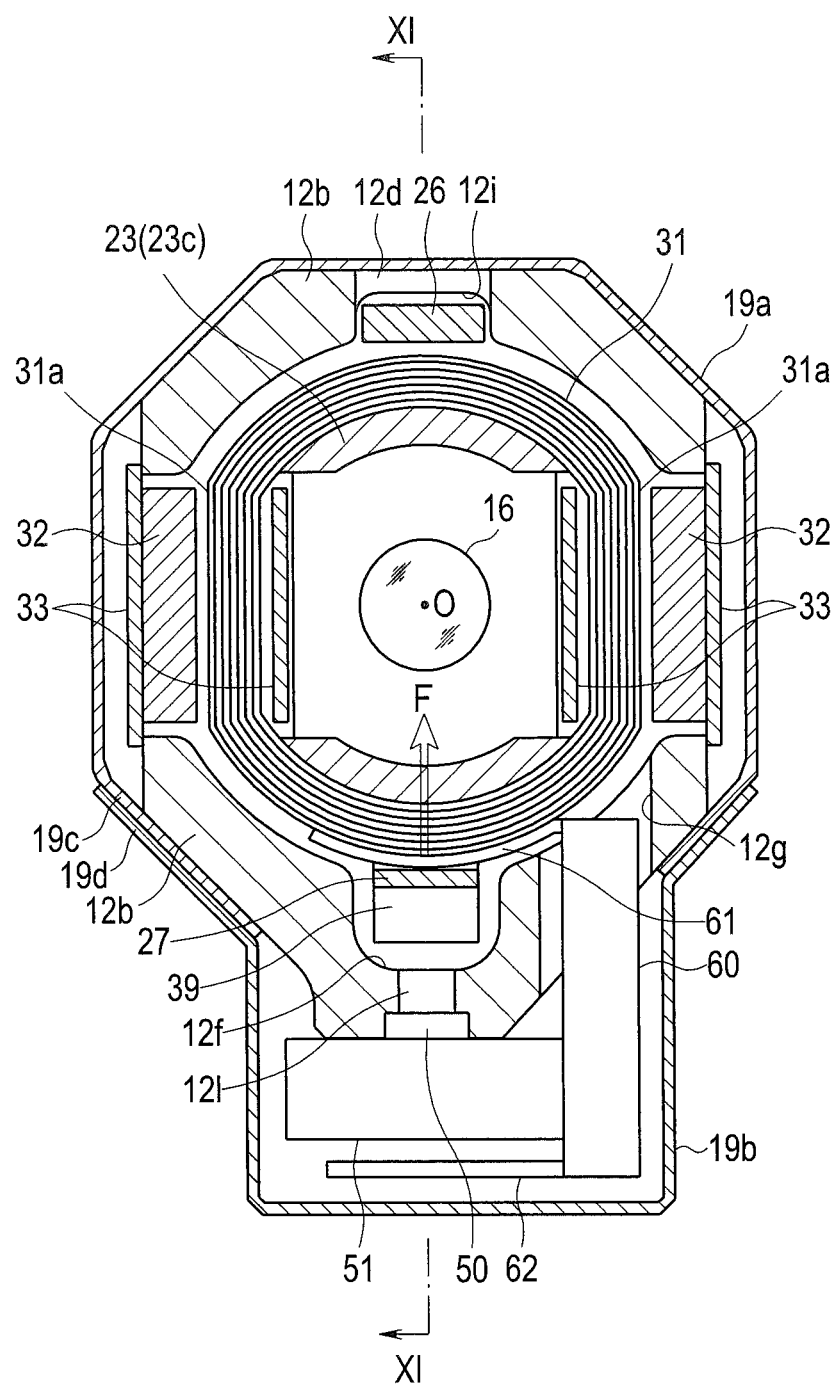
FIG. 10 is a lateral section showing the configuration of the image pickup unit.
Figure 11:
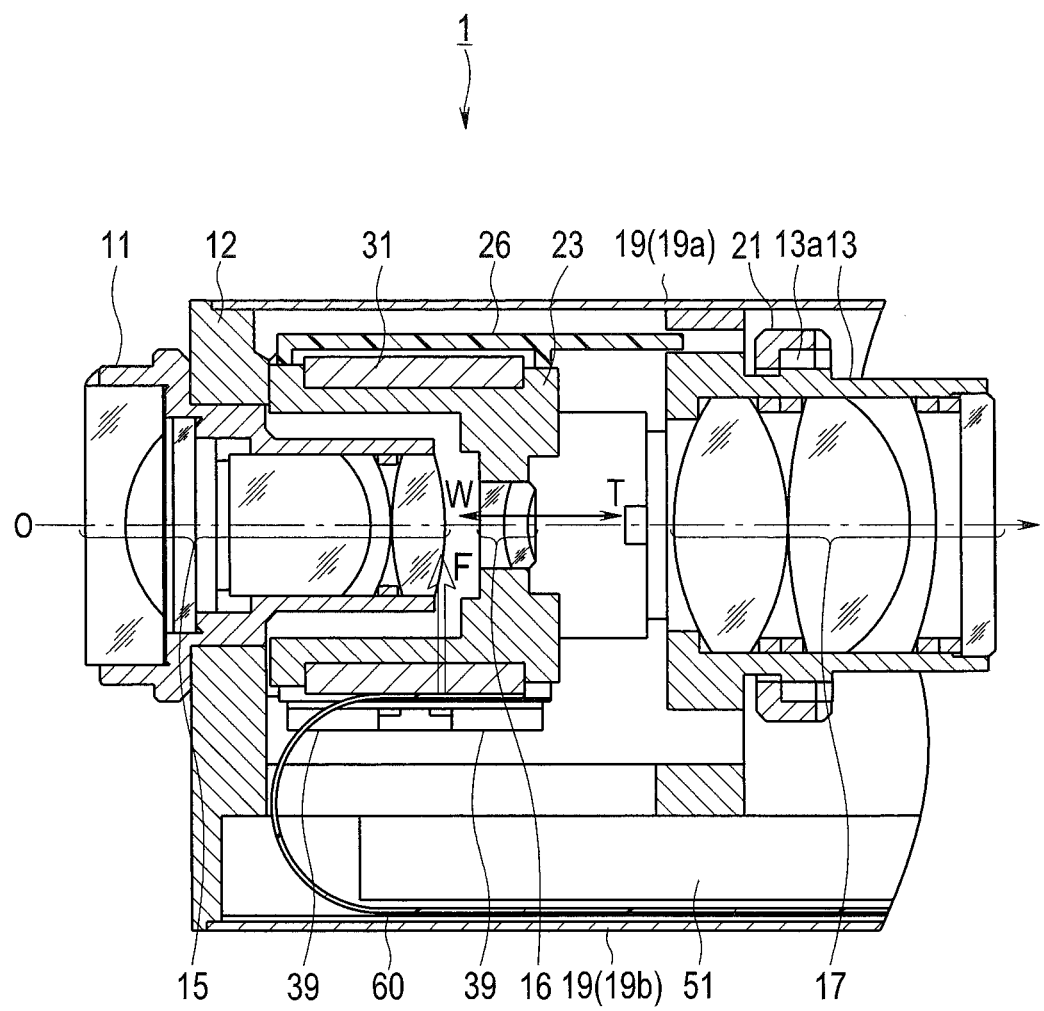
FIG. 11 is a longitudinal section showing the image pickup unit along line XI-XI of FIG. 10.

FIG. 1 is a diagram showing a configuration of an endoscope. FIG. 2 is a longitudinal section showing a configuration of an image pickup unit in a longitudinal direction. FIG. 3 is a longitudinal section showing the configuration of the image pickup unit in a longitudinal direction different from that of FIG. 2. FIG. 4 is a perspective view showing configurations of a fixed barrel and a shield cover. FIG. 5 is a perspective view showing the configuration of the shield cover. FIG. 6 is a perspective view showing a configuration of a moving lens drive unit. FIG. 7 is an exploded perspective view showing the configuration of the moving lens drive unit. FIG. 8 is a side view showing a state of a moving lens drive unit disposed in the fixed barrel. FIG. 9 is a bottom view showing the moving lens drive unit disposed in the fixed barrel. FIG. 10 is a lateral section showing the configuration of the image pickup unit. FIG. 11 is a longitudinal section showing the image pickup unit along line XI-XI of FIG. 10.

An example of the embodiment according to the present invention will be described below. Referring to FIG. 1, a configuration example of an endoscope 101 including an image pickup unit 1 according to the present invention will be first discussed below. The endoscope 101 of the present embodiment can be introduced into a subject such as a human body and is configured to optically pick up an image of a predetermined observation portion in the subject. Note that the endoscope 101 may be introduced into living bodies other than human bodies, or man-made structures such as a machine and a building.

The endoscope 101 mainly includes an insertion section 102 that is introduced into a subject, an operation section 103 positioned on a proximal end of the insertion section 102, and a universal code 104 serving as a composite cable extending from a side of the operation section 103.

The insertion section 102 includes a distal end portion 110 disposed on a distal end of the insertion section 102, a bending portion 109 disposed in a bendable manner on a proximal end side of the distal end portion 110, and a flexible tube portion 108 having flexibility that is disposed on a proximal end side of the bending portion 109 and is connected to a distal end side of the operation section 103 such that the distal end portion 110, the bending portion 109, and the tube portion 108 are connected to one another. Note that the endoscope 101 may be configured like a so-called rigid endoscope in which the insertion section 102 does not have a flexible portion.

As will be specifically discussed later, the distal end portion 110 has the image pickup unit 1. Moreover, the operation section 103 has an angle operation knob 106 for a bending operation of the bending portion 109. The operation section 103 has a zooming portion 107 that is a lever switch that provides an operation instruction for a voice coil motor portion 30, which will be discussed later, and performs a zooming operation of the image pickup unit 1. Note that the zooming portion 107 may be switches of other types, e.g., a volume switch or a push switch.

An endoscope connector 105 connected to an outside apparatus 120 is provided on a proximal end portion of the universal code 104. The outside apparatus 120 connected to the endoscope connector 105 includes, for example, a light source unit, an image processing unit, and an image display unit 121 such as a monitor.

The endoscope 101 includes an electric cable 115 that is inserted into the universal code 104, the operation section 103, and the insertion section 102 and an optical fiber bundle (not shown) that transmits illuminating light from the light source unit provided in the outside apparatus 120.

The electric cable 115 is configured to electrically connect the connector portion 105 and the image pickup unit 1. The connector portion 105 connected to the outside apparatus 120 electrically connects the image pickup unit 1 to the outside apparatus 120 via the electric cable 115. The electric cable 115 allows power supply from the outside apparatus 120 to the image pickup unit 1 and communications between the outside apparatus 120 and the image pickup unit 1.

The outside apparatus 120 includes a motor drive control unit 120a and an image processing unit 120b. The motor drive control unit 120a is configured to control driving of a voice coil motor portion 30, which will be specifically described later, in the image pickup unit 1.

The image processing unit 120b is configured to generate a video signal based on an image pickup device output signal outputted from the image pickup unit 1 and output the video signal to the image display unit 121. Namely, in the present embodiment, an optical image picked up by the image pickup unit 1 is displayed as video on the image display unit 121. Note that the image processing unit and the image display unit 121 may be partially or entirely provided in the endoscope 101.

The optical fiber bundle is configured to transmit light from the light source unit of the outside apparatus 120 to an illuminating window serving as an illuminating light emitting portion of the distal end portion 110. Note that the light source unit may be disposed in one of the operation section 103 and the distal end portion 110 of the endoscope 101.

A configuration of the image pickup unit 1 provided in the distal end portion 110 will be described below.

In the following explanation, a direction from the image pickup unit 1 toward an object along an optical axis O of shooting light (to left in FIGS. 2 and 3) will be called a forward direction (an object side) while an opposite direction will be called a rearward direction (an image side).

As shown in FIGS. 2 and 3, the image pickup unit 1 of the present embodiment includes, sequentially from an object side in the forward direction, a front group lens holding barrel 11 as a first lens holding barrel, a fixed barrel 12 as a second lens holding barrel, a rear group lens holding barrel 13 as a third lens holding barrel, and an image pickup device holding barrel 14. The front group lens holding barrel 11, the fixed barrel 12, the rear group lens holding barrel 13, and the image pickup device holding barrel 14 are fitted together by, for example, press fitting, and are fixed to one another with an adhesive or the like.

The front group lens holding barrel 11 holds a front group lens 15 as a first objective optical system. The fixed barrel 12 stores a moving lens holding barrel 23 so as to freely advance and retract the moving lens holding barrel 23. The moving lens holding barrel 23 holds a moving lens 16 as a second objective optical system and advances and retracts along the optical axis O. The rear group lens holding barrel 13 holds a rear group lens 17 as a third objective optical system. Note that detailed configurations of the fixed barrel 12 and the moving lens holding barrel 23 will be discussed later.

The image pickup device holding barrel 14 holds an optical member 18 that is a transparent cover body for protecting a light receiving portion of the image pickup device 10. The image pickup device 10 is bonded to a rear surface of the image pickup device holding barrel 14. In the image pickup device 10, an image pickup substrate portion 10a to be mounted is connected to an image pickup cable 53. The image pickup cable 53 is inserted and stored in the electric cable 115 shown in FIG. 1.

Note that in the image pickup device 10, a plurality of devices that output an electric signal according to incident light at a predetermined time are disposed on the flat light receiving portion. For example, a typical image pickup device called a CCD (charge-coupled device) or a CMOS (complementary metal oxide semiconductor) sensor or other kinds of image pickup devices may be used. The image pickup device 10 is disposed such that the light receiving portion is located on an image forming surface of an objective lens group including the front group lens 15, the moving lens 16, and the rear group lens 17.

The image pickup unit 1 includes a shield cover 19 composed of a metallic plate for keeping internal watertightness and electromagnetic shielding. A distal end portion of the shield cover 19 is fixed to an outer barrel portion of the fixed barrel 12 so as to form an outer sheath of the image pickup unit 1. In the image pickup unit 1, internal watertightness is kept by injecting a filling agent 54 such as an adhesive to a midpoint of the image pickup device holding barrel 14 in a rear end portion of the shield cover 19. Note that a detailed configuration of the shield cover 19 will be described below.

Moreover, a convex portion 13a having a screw groove is provided on an outer periphery of the rear group lens holding barrel 13. An adjusting ring 21 is screwed to the convex portion 13a so as to adjust a moving position in the rearward direction according to an amount of screwing.

The adjusting ring 21 comes into contact with a rear end face of a plate-like rotation restricting portion 26, which will be discussed later, so as to regulate a rearward movement of the moving lens holding barrel 23. A front surface portion of the rotation restricting portion 26 is provided on the moving lens holding barrel 23. This configuration adjusts an amount of rearward movement of the moving lens holding barrel 23, leading to an adjustment of a lens stroke of the moving lens 16.

In the present embodiment, for example, a shooting magnification is maximized when the moving lens 16 is located at a rearmost position of a movable range, whereas the shooting magnification is minimized when the moving lens 16 is located at a foremost position of the movable range. In other words, a focal length is minimized with a wide field of view, that is, a state of a so-called wide end when the moving lens 16 is located at the foremost position, whereas the focal length is maximized with a narrow field of view, that is, a state of a so-called tele end when the moving lens 16 is located at the rearmost position. Namely, the moving lens 16 is placed into the state of the tele end when a rear end portion of the rotation restricting portion 26 provided on the moving lens holding barrel 23 is located at a rearmost position where the rear end portion is stopped into contact with the adjusting ring 21.

The detailed configurations of the fixed barrel 12 and the shield cover 19 will be described below.

As shown in FIG. 4, the fixed barrel 12 includes a plate-like front surface portion and an outer rectangular cylindrical portion 12b that is extended from an upper portion and a lower middle portion of the front surface portion 12a to the rear side. The front surface portion 12a of the fixed barrel 12 has a hole portion 12c bored therein where the front group lens holding barrel 11 is insertedly fitted.

The moving lens drive unit 20 (see FIGS. 6 and 7), which will be described later, is fixed to the cylindrical portion 12b of the fixed barrel 12 such that the moving lens holding barrel 23 of the moving lens drive unit 20 can freely advance and retract in the cylindrical portion 12b. Note that the moving lens holding barrel 23 is disposed so as to slide along the optical axis O while a rotation of the moving lens holding barrel 23 about the optical axis O is regulated in the cylindrical portion 12b of the fixed barrel 12.

A long hole 12d is longitudinally formed on an upper flat portion of the cylindrical portion 12b of the fixed barrel 12. Furthermore, a concave portion 12e is formed that communicates with the long hole 12d and linearly guides the plate-like rotation restricting portion 26, which will be described later, provided on the moving lens holding barrel 23.

Inside a lower flat portion of the cylindrical portion 12b, a concave portion 12f is formed so as to advance and retract a position detecting magnet 39, which will be described later, provided on the moving lens holding barrel 23. Moreover, on one lower inclined portion of the cylindrical portion 12b, an FPC insertion hole portion 12g is formed as a long hole for insertion of a flexible printed circuit board (hereafter, will be called an FPC) 60, which will be described later, as a circuit board that supplies power to the voice coil motor portion 30.

A pair of permanent magnet storage portions 12h are formed like slits on right and left sides of the cylindrical portion 12b so as to longitudinally divide the cylindrical portion 12b into two upper and lower sections. Permanent magnets 32 of the voice coil motor portion 30 are disposed in the pair of permanent magnet storage portions 12h (see FIG. 2). Note that the permanent magnet storage portions 12h are disposed with line symmetry relative to the optical axis O serving as a symmetry axis.

A fitting concave portion 12i, into which a distal end portion of the rear group lens holding barrel 13 is fit, is formed on an inner surface of a rear portion of the cylindrical portion 12b. Moreover, a long groove 12j, which is not shown in FIG. 4, is formed where a magnetism detecting portion 50 faces the upper flat portion of the cylindrical portion 12b together with position detecting magnets 39 so as to have a predetermined clearance in a direction orthogonal to the optical axis O (see FIG. 9).

The shield cover 19 is fixed to the fixed barrel 12 configured as described above. The shield cover 19 covers the cylindrical portion 12*b* along an outside shape of the front surface portion 12*a* and is extended to a rear side so as to form the outer sheath of the image pickup unit 1. As shown in FIG. 5, the shield cover 19 includes two metallic plate members: a first cover body 19*a* covering an upper side of the fixed barrel 12 and a second cover body 19*b* covering a lower side of the fixed barrel 12.

The shield cover 19 is bonded and fixed such that an inclined face portion 19*d* on the upper side of the second cover body 19*b* is superimposed on an inclined face portion 19*c* on the lower side of the first cover body 19*a* when the shield cover 19 is assembled to the fixed barrel 12. The first cover body 19*a* of the shield cover 19 covers an outer surface on the upper side of the cylindrical portion 12*b* and has a distal end portion that is bonded to the front surface portion 12*a*.

The second cover body 19*b* of the shield cover 19 has a distal end portion that is bonded to the front surface portion 12*a* and forms a space section where a rigid substrate 51 and an FPC 60 are stored on the lower side of the cylindrical portion 12*b*. The second cover body further has a pair of rectangular cable holders 19*e* that protrude from both proximal end sides of the second cover body. The pair of cable holders 19*e* are each folded inward to fix a control cable 52 by crimping.

A detailed configuration of the moving lens drive unit 20 will be described below.

As shown in FIGS. 6 and 7, the moving lens drive unit 20 of the present embodiment includes the rotation restricting portion 26, the moving lens holding barrel 23 that has the position detecting magnet 39 and the position detecting magnet holding portion 27 and holds the moving lens 16, the voice coil motor portion 30, the rigid substrate 51, and the FPC 60.

The moving lens holding barrel 23 is a substantially cylindrical member that advances or retracts along the optical axis O and holds the moving lens 16 in the moving lens holding barrel 23. The moving lens holding barrel 23 includes a lens holding portion 23*a*, front and rear sliding portions 23*b* that are flanged outward, coil winding portions 23*c* that are two upper and lower portions provided between the front and rear sliding portions 23*b* so as to extend forward, and notch portions 23*d* for division of the upper and lower sliding portions 23*b* and the upper and lower coil winding portions 23*c*.

The lens holding portion 23*a* has a through hole bored thereon along the optical axis O. The moving lens 16 is fixed in the through hole.

The plate-like rotation restricting portion 26 is fit onto the sliding portions 23*b*. The position detecting magnet holding portion 27 is fixed under the sliding portions 23*b*. The position detecting magnet holding portion 27 is fit across bottoms of the front and rear sliding portions 23*b* with a predetermined clearance from a coil portion 31 of the voice coil motor portion 30.

In this configuration, the two position detecting magnets 39 are fixed to an undersurface of the position detecting magnet holding portion 27. Specifically, the two position detecting magnets 39 are disposed along the optical axis O (longitudinal direction) on the undersurface of the position detecting magnet holding portion 27. In the present embodiment, for example, the front position detecting magnet 39 has a north pole near the position detecting magnet holding portion 27 and a south pole on an opposite side of the magnet, whereas the rear position detecting magnet 39 has a south pole near the position detecting magnet holding portion 27 and a north pole on an opposite side of the magnet.

The position detecting magnet holding portion 27 is disposed at a position shifted by 180° in a circumferential direction relative to the rotation restricting portion 26. Namely, the position detecting magnet holding portion 27 is located with point symmetry about a point on the optical axis O from the rotation restricting portion 26, and is disposed on an opposite side of the optical axis O from the rotation restricting portion 26. Note that a weight of the rotation restricting portion 26 is set substantially equal to a total weight of the position detecting magnet holding portion 27 and the two position detecting magnets 39, vertically keeping weight balance of the moving lens holding barrel 23 extended along the optical axis O (that is, a barycenter is located on the optical axis O). This configuration suppresses an inclination of the moving lens holding barrel 23 relative to the optical axis O in the fixed barrel 12.

The magnetism detecting portion 50 is disposed at a position facing the two position detecting magnets 39. The magnetism detecting portion 50 includes a Hall device and a magnetoresistance device (MR device) and can detect a magnetic field of the position detecting magnet 39. The magnetism detecting portion 50 is disposed on the rigid substrate 51 that is fixed to the fixed barrel 12 with an adhesive or the like.

The magnetism detecting portion 50 is electrically connected to the motor drive control unit 120*a* of the outside apparatus 120 shown in FIG. 1 via the control cable 52 (see FIG. 3) connected to a connecting terminal (not shown), which is provided on a top surface of a rear portion of the rigid substrate 51, with solder or the like. Note that the control cable 52 is inserted and stored with the image pickup cable 53 into the electric cable 115 shown in FIG. 1.

The magnetism detecting portion 50 detects a changes of a magnetic field generated by relative movement of the position detecting magnets 39, which are provided on the moving lens holding barrel 23, in the longitudinal direction along the optical axis O. The motor drive control unit 120*a* shown in FIG. 1 calculates a position of the position detecting magnet 39 in the direction of the optical axis O, that is, a position of the moving lens holding barrel 23 according to the change of the magnetic field detected by the magnetism detecting portion 50.

The voice coil motor portion 30 is a driving portion (driving means) that generates a driving force for advancing and retracting the moving lens holding barrel 23 in the longitudinal direction along the optical axis O in response to an operation of the zooming portion 107 shown in FIG. 1.

Specifically, as shown in FIGS. 6 and 7, the voice coil motor portion 30 includes the coil portion 31 wound around the coil winding portions 23*c* of the moving lens holding barrel 23, the pair of permanent magnets 32, and a pair of yokes 33. The voice coil motor portion 30 has a configuration of a so-called moving-coil voice coil motor. Note that a principle of the voice coil motor is well known and thus a detailed explanation thereof is omitted.

The coil portion 31 includes lead wires wound around the coil winding portions 23*c* of the moving lens holding barrel 23. The coil portion 31 is substantially linearly wound at a point located outside of the pair of notch portions 23*d* in a radial direction, the notch portions 23*d* being formed on both sides of the moving lens holding barrel 23. Note that the point where the coil portion 31 is linearly wound looks substantially planar, and thus the point will be called a flat portion 31*a* of the coil portion 31.

The pair of permanent magnets 32 and the pair of yokes 33 form a magnetic circuit that generates a magnetic field in a direction orthogonal to the flat portion 31a of the coil portion 31. Note that in the present embodiment, for example, the pair of permanent magnets 32 are disposed with a north pole located on an inner surface (facing the optical axis O) of the permanent magnet 32 in the radial direction and a south pole located on an outer surface (opposite from the optical axis O) of the permanent magnet 32 in the radial direction.

Furthermore, the yoke 33 having a magnetic body is disposed on the outer surface of the pair of permanent magnets 32 in the radial direction. The yokes 33 are inserted into a clearance formed inside the coil portion 31 in the radial direction such that the yoke 33 longitudinally covers both ends of the permanent magnet 32. Note that the yokes 33 are disposed so as not to interfere with the coil portion 31 when the moving lens holding barrel 23 advances or retracts in the fixed barrel 12.

As has been discussed, the flat portions 31a of the coil portion 31 surrounded by the permanent magnets 32 and the yokes 33 are placed in a magnetic field in a direction orthogonal to the flat portions 31a. Namely, the permanent magnets 32 and the yokes 33 generate a magnetic field orthogonal to a winding direction of the lead wire in the flat portion 31a of the coil portion 31. Thus, the voice coil motor portion 30 of the present embodiment controls a current applied to the coil portion 31, thereby generating a driving force for moving the moving lens holding barrel 23 along the optical axis O.

Note that the voice coil motor portion 30 is configured to receive power supplied from the FPC 60 described above. The FPC 60 includes a coil connection portion 61 having a connection terminal at a front side of the coil connection portion 61 connected to the lead wire of the coil portion 31 with solder or the like, and a cable connection portion 62 having a connection terminal at a rear side of the cable connection portion 62 connected with solder or the like to a wiring cable disposed in the control cable 52 (see FIG. 3).

The coil connection portion 61 and the cable connection portion 62 are widely formed so as to extend in the direction of one side of the FPC 60. Note that the coil connection portion 61 is connected to the lead wire of the coil portion 31, is disposed in a clearance formed between the coil portion 31 and the position detecting magnet holding portion 27, and then is bonded and fixed to a circumferential portion under the coil portion 31.

As has been discussed, in this configuration, the rectangular magnetism detecting portion 50 is disposed on a top surface portion of one end side of the rigid substrate 51. The rectangular magnetism detecting portion 50 detects a magnetic field of the position detecting magnets 39. Note that the magnetism detecting portion 50 needs to be accurately positioned with respect to the position detecting magnets 39 and thus is opposed to the position detecting magnets 39 with a predetermined clearance.

In the moving lens drive unit 20 configured as above, as shown in FIGS. 8 and 9, the pair of yokes 33 of the voice coil motor portion 30 are fixed to both side portions of the fixed barrel 12. Specifically, both flat portions having the permanent magnet storage portions 12h and the longitudinal edge side portions of the pair of yokes 33 overlap each other and are fixed with an adhesive such that the permanent magnets 32 are stored in the permanent magnet storage portions 12h of the fixed barrel 12.

Note that the pair of permanent magnets 32 stored in the permanent magnet storage portions 12h are fixed to the yokes 33 with an adhesive or a magnetic force. As shown in FIG. 10, the pair of permanent magnets 32 and the pair of yokes 33 are fixed at positions with point symmetry about a point of the optical axis O.

The FPC 60 is inserted into the FPC insertion hole portion 12g formed on the cylindrical portion 12b of the fixed barrel 12, and a front side of the FPC 60 is bent into an arc shape and is deformed to extend rearward along an undersurface of the rigid substrate 51. In other words, the FPC 60 is disposed in a clearance formed between the undersurface of the rigid substrate 51 and an inner surface of the second cover body 19b on a lower side of the shield cover 19.

The rigid substrate 51 is bonded and fixed to the undersurface of the cylindrical portion 12b of the fixed barrel 12. In this case, as shown in FIG. 9, the rigid substrate 51 is bonded and fixed to the cylindrical portion 12b of the fixed barrel 12 such that a front end face and one side face of the rectangular magnetism detecting portion 50 are in surface contact with a right-angled positioning surface 12k formed at a front of the long groove 12j in a lower portion of the cylindrical portion 12b of the fixed barrel 12. Thus, the magnetism detecting portion 50 is accurately positioned with respect to the position detecting magnets 39.

Note that, in order to increase detection accuracy of a magnetic field detected from the position detecting magnet 39 by the magnetism detecting portion 50, the long groove 12j in the lower portion of the cylindrical portion 12b of the fixed barrel 12 has a through hole 12l at a position where the magnetism detecting portion 50 and the position detecting magnets 39 are opposed to each other.

As has been discussed, as shown in FIG. 10, the moving lens drive unit 20 of the present embodiment include the yokes 33 that are bonded and fixed to both sides of the fixed barrel 12 such that the permanent magnets 31 of the voice coil motor portion 30 are stored in the permanent magnet storage portions 12h formed on the fixed barrel 12. Thus, the permanent magnets 32 and the yokes 33 are substantially stored in the fixed barrel 12.

The moving lens holding barrel 23 has the notch portions 23d formed in regions located inside of the permanent magnets 32 in the radial direction. The coil portion 31 having the flat portions 31a is formed on the notch portion 23d by winding the lead wires. The flat portions 31a are located inside of the outside diameter of the coil portion 31. Thus, in the present embodiment, the permanent magnets 32 and the yokes 33 can be disposed inward in the radial direction, thereby reducing a size of the voice coil motor portion 30.

The size reduction of the voice coil motor portion 30 can miniaturize the moving lens drive unit 20. Consequently, the image pickup unit 1 of the present embodiment can be also reduced in size, achieving the endoscope 101 provided with the thinner distal end portion 110 of the insertion section 102.

However, the size reduction of the voice coil motor portion 30 of the moving lens drive unit 20 reduces power for advancing and retracting the moving lens holding barrel 23. Thus, as shown in FIGS. 10 and 11, the moving lens holding barrel 23 in the image pickup unit 1 according to the present embodiment is always pressed upward by a reaction force F of the bent FPC 60 via the coil portion 31 of the voice coil motor portion 30. Namely, the moving lens holding barrel 23 is pressed in a direction orthogonal to the optical axis O, that is, upward from a lower part of FIG. 10 by the reaction force F of the FPC 60. Thus, a part of outer surfaces of the sliding portions 23b provided at front and rear of the moving lens holding barrel 23 is always partially pressed to an inner surface of the fixed barrel 12 in an urging direction.

With this configuration, the moving lens holding barrel 23 not inclined with respect to the optical axis O prevents so-called prying or the like and is always kept in a certain orientation with respect to the optical axis O in the fixed barrel 12. Consequently, the moving lens holding barrel 23 can smoothly advance and retract along the optical axis O in the fixed barrel 12.

Note that the FPC 60 requires a certain arc shape to urge the moving lens holding barrel 23. The image pickup unit 1 may increase in size depending on an extending direction of the FPC 60. Thus, in the present embodiment, the coil connection portion 61 is bonded to the bottom of the coil portion 31 provided on the moving lens holding barrel 23 and is extended rearward along the undersurface of the rigid substrate 51 from a position shifted in the radial direction of the moving lens holding barrel 23. This prevents a size increase of the image pickup unit 1.

According to the explanation, in the image pickup unit 1 of the present embodiment, even the low-power voice coil motor portion 30 can smoothly advance and retract the moving lens holding barrel 23 without causing defective sliding of the moving lens holding barrel 23.

Moreover, in the image pickup unit 1, the moving lens holding barrel 23 that advances and retracts is kept in a certain orientation in the fixed barrel 12 in response to the urging force F from the FPC 60, thereby stably keeping a position of the moving lens 16 along the optical axis O. This advantageously stabilizes optical performance such as a zooming function of the image pickup unit 1.

Note that for example, the image pickup device 10 of the image pickup unit 1 according to the present embodiment is set such that the moving lens holding barrel 23 is urged by of the FPC 60 in the same direction as an upward direction of an observation image of received light. Namely, the image pickup device 10 is set such that the FPC 60 urges the lens holding barrel 23 in the same direction as an upper side of an observation image displayed on the image display unit 121.

In many cases, the endoscope 101 is inserted into a subject such that the insertion section 102 is oriented with an observation image vertically aligned with a vertical direction of the insertion section 102. At this point, the FPC 60 urges the moving lens holding barrel 23 against a gravity direction (vertically downward). This allows the FPC 60 to urge the moving lens holding barrel 23 in a direction that cancels weights of the coil portion 31 of the voice coil motor portion 30, the rotation restricting portion 26, and the moving lens holding barrel 23 including the position detecting magnet holding portion 27 and the two position detecting magnets 39.

Thus, when the distal end portion 110 of the insertion section 102 is oriented along the vertical direction of the observation image displayed on the image display unit 121, a sliding resistance of the moving lens holding barrel 23 advantageously decreases against the fixed barrel 12.

Even if a bending operation of the bending portion 109 provided in the insertion section 102 causes an acceleration on the image pickup unit 1, the FPC 60 always urges the moving lens holding barrel 23 in one direction and thus stably advances and retracts the moving lens holding barrel 23.

As has been discussed, the moving lens holding barrel 23 includes the two position detecting magnets 39. The two position detecting magnets 39 are opposed to the lower second cover body 19*b* of the shield cover 19 composed of a metallic plate of a magnetic body and the position detecting magnets 39 are attracted to the second cover body 19*b*. On the contrary, the FPC 60 urges the moving lens holding barrel 23 in one direction against a magnetic force for attracting the two position detecting magnets 39 to the second cover body 19*b*. Thus, the moving lens holding barrel 23 can stably advance and retract because of a reduction in sliding resistance against the fixed barrel 12. Furthermore, a clearance between the two position detecting magnets 39 and the magnetism detecting portion 50 is kept in a direction orthogonal to the optical axis O, advantageously allowing the magnetism detecting portion 50 to stably detect a position of the moving lens holding barrel 23.

Note that in order to obtain the optimum reaction force F that urges the moving lens holding barrel 23 in one direction, a material, a thickness, and a width of the FPC 60 are set according to weights of the coil portion 31 of the voice coil motor portion 30, the rotation restricting portion 26, the position detecting magnet holding portion 27, and the moving lens holding barrel 23 including the two position detecting magnets 39. The urging force F of the FPC 60, in particular, is preferably set to be proportional to the weights of the coil portion 31, the rotation restricting portion 26, the position detecting magnet holding portion 27, and the moving lens holding barrel 23 including the two position detecting magnet 39.

The present invention is not limited to the foregoing embodiment. The present invention can be optionally changed within a scope or idea of the invention so as to be understandable from claims and a specification of the invention. Image pickup units and endoscopes involving such a change also fall within a technical scope of the present invention.

What is claimed is:

1. An image pickup unit having an objective optical system that forms an object image,
the image pickup unit comprising:
a moving lens constituting a part of the objective optical system;
a moving lens holding barrel for holding the moving lens, the moving lens holding barrel being disposed so as to freely advance and retract along a shooting optical axis that enters the objective optical system;
a fixed barrel that stores and holds the moving lens holding barrel so as to freely advance and retract;
a drive unit serving as a voice coil motor portion that generates a driving force for advancing and retracting the moving lens holding barrel along the shooting optical axis in the fixed barrel, the drive unit including a coil wound about the optical axis around the moving lens holding barrel, and a permanent magnet fixed to the fixed barrel;
a flexible substrate for power supply to the drive unit, the flexible substrate being disposed so as to urge the moving lens holding barrel in one direction orthogonal to the shooting optical axis and bent so as to press a part of an outer surface of the moving lens holding barrel in the one direction to an inner surface of the fixed barrel;
a position detecting magnet fixed to the moving lens holding barrel; and
a magnetism detecting portion opposed to the position detecting magnet with a predetermined clearance in a direction orthogonal to the optical axis, the magnetism detecting portion detecting a relative position of the moving lens holding barrel from the fixed barrel according to magnetism of the position detecting magnet, the flexible substrate urging the moving lens holding barrel in the one direction so as to keep the predetermined clearance between the position detecting magnet and the magnetism detecting portion.

2. The image pickup unit according to claim 1, further comprising a shield cover disposed so as to cover the fixed barrel along an outside shape of the fixed barrel, the moving lens holding barrel being urged in the one direction against a direction orthogonal to the optical axis along which the position detecting magnet is attracted to the shield cover by a magnetic force.

3. An endoscope comprising the image pickup unit according to claim 1.

\* \* \* \* \*